United States Patent
Qiu et al.

(10) Patent No.: US 10,564,075 B2
(45) Date of Patent: Feb. 18, 2020

(54) PREFIXATION FOR INCREASED RARE CELL RECOVERY

(71) Applicant: Siemens Healthcare Diagnostics Inc., Tarrytown, NY (US)

(72) Inventors: Xiaolei Qiu, San Ramon, CA (US); Sunil Pandit, Danville, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/553,529

(22) PCT Filed: Feb. 23, 2016

(86) PCT No.: PCT/US2016/019016
§ 371 (c)(1),
(2) Date: Aug. 24, 2017

(87) PCT Pub. No.: WO2016/137915
PCT Pub. Date: Sep. 1, 2016

(65) Prior Publication Data
US 2018/0238779 A1    Aug. 23, 2018

Related U.S. Application Data

(60) Provisional application No. 62/119,922, filed on Feb. 24, 2015.

(51) Int. Cl.
*G01N 1/30* (2006.01)
*G01N 1/40* (2006.01)
(Continued)

(52) U.S. Cl.
CPC .............. *G01N 1/30* (2013.01); *B01D 61/147* (2013.01); *B01D 61/18* (2013.01); *C12Q 1/68* (2013.01);
(Continued)

(58) Field of Classification Search
None
See application file for complete search history.

(56) References Cited

U.S. PATENT DOCUMENTS

2013/0316347 A1    11/2013   Brechot et al.
2015/0314290 A1*  11/2015   Cho .................... B01L 3/50273
                                                                 435/6.12

FOREIGN PATENT DOCUMENTS

WO    2003018757 A2    3/2003

OTHER PUBLICATIONS

Cahill, Mr; et al; "Fixation with formaldehyde induces expression of activation dependent platelet membrane glycoproteins, P selectin (CD62) and GP53 (CD63)" British Journal of Haematology, 84, 527-529, 1993 (Year: 1993).*

(Continued)

*Primary Examiner* — David W Berke-Schlessel

(57) ABSTRACT

Traditionally, enriching or isolating rare circulating cells from a sample has proven difficult as rare circulating cells can be heterogeneous, which limits the use of techniques based on biological properties (e.g., cell surface markers), and can be flexible, which hinders techniques based on physical properties (e.g., diameter size). Methods disclosed herein are capable of enriching or isolating rare circulating cells are minimally impacted by heterogeneity or flexibility of rare circulating cells, and therefore, overcome disadvantages observed with prior techniques. For example, a method for enriching or isolating rare circulating cells from a sample of a subject including fixing one or more rare circulating cells in a sample to create a fixed sample, and isolating the one or more rare circulating cell from the fixed sample using a size exclusion technique is disclosed.

15 Claims, 2 Drawing Sheets

(51) Int. Cl.
- *B01D 61/14* (2006.01)
- *B01D 61/18* (2006.01)
- *G01N 33/574* (2006.01)
- *C12Q 1/68* (2018.01)
- *G01N 33/50* (2006.01)

(52) U.S. Cl.
CPC ....... *G01N 1/4077* (2013.01); *G01N 33/5005* (2013.01); *G01N 33/574* (2013.01); *G01N 2001/305* (2013.01); *G01N 2001/4088* (2013.01)

(56) References Cited

OTHER PUBLICATIONS

International Search Report for PCT/US2016/019016 dated Jun. 9, 2016.

Tseng et al., Dynamic Changes in Numbers and Properties of Circulating Tumor Cells and Their Potential Applications. Cancers (Basel). 2014, vol. 6(4), p. 2369-2386.

Lin et al., Portable Filter-Based Microdevice for Detection and Characterization of Circulating Tumor Cells. Clin Cancer Res. 2010, vol. 16(20), p. 5011-8.

Harouaka et al., Circulating tumor cell enrichment based on physical properties. J Lab 1-5, 18-19 Autom. 2013, vol. 18(6), p. 455-468.

Vona, Giovanna et al.: "Isolation by Size of Epithelial Tumor Cells: A New Method for the Immunomorphological and Molecular Characterization of Circulating Tumor Cells" in: American Journal of Pathology; Elsevier, Inc., US; vol. 156; No. 1; Jan. 1, 2000; pp. 57-63; XP002186868; ISSN: 0002-9440 / Jan. 1, 2000.

De Jongste, Adriaan H. et al: "Use of Transfix(TM) Cerebrospinal Fluid Storage Tubes Prevents Cellular Loss and Enhaces Flow Cytometric Detection of Malignant Hematological Cells After 18 ours of Storage: Transfix(TM) for CSF Flow Cytometry"; Cytometry; Part B, Clinical Cytometry; vol. 86; No. 4, May 14, 2013; pp. 272-279; XP055426249; US ISSN: 1552:4949; DOI: 10.1002/cyto.b.21097 / May 14, 2013.

Fasching, Peter A. et al.: "4EVER: Assessment of circulating tumor cells with a novel, filtration-based method, in aphase IIIb multi-center study for post menopausal, HER2-negative, estrogen receptor-positive, advanced breast cancer patients"; Jan. 1, 2013; pp. 1-2; XP055426218; DOI: 10.13140/RG.2.1.3454.8328; retrieved from Internet on Nov. 17, 2017-URL-address see Search Report / Jan. 1, 2013.

Dorsey, Jay F. et al; "Tracking viable circulating tumor cells (CTCs) in the peripheral blood of non-small cell lung cancer (NSCLC) patients undergoing definitive radiation therapy: Pilot study results"; Cancer; vol. 121; No. 1; pp. 139-149; XP055494177; ISSN: 0008-543X; DOI: 10.1002/cncr.28975 / Sep. 19, 2014.

Supplementary European Search Report for EP Application No. 16756139.8 dated Nov. 29, 2017.

* cited by examiner

PREFIXATION FOR INCREASED RARE CELL RECOVERY

BACKGROUND

Cancer can start in any organ or tissue in the body. A primary cancer or tumor is a first, original tumor that develops in the body. A metastatic cancer or tumor occurs when cancer cells spread from a primary tumor to a new part of the body. In other words, metastatic tumors always start from cancer cells in another part of the body. For example, breast cancer can spread from its primary site (i.e., a breast) to form a new tumor in a different part of the body, such as bones. Cancer cells in a second bone tumor are the same as cells in the primary breast tumor—i.e., cells are breast cancer cells, and not bone cancer cells.

Cancer spreads from a primary tumor to other parts of the body via circulating tumor cells (CTCs). CTCs arise from primary or secondary tumors and are shed into the vasculature system from the tumors. CTCs travel in blood or lymph fluid to distant sites to form metastasis after gaining properties of extravasation, survival and proliferation in a target tissue.

SUMMARY

Compositions and methods disclosed herein encompass the discovery that fixing rare circulating cells in a sample from a subject increases a recovery rate of rare circulating cells from a sample. Rare circulating cells can be recovered from a sample using, for example, size exclusion techniques (e.g., filtration). However, cells are elastic, and a cell can pass through a pore having a diameter smaller than a diameter of a cell, which, in turn, can compromise recovery. Without being bound to any theory, fixation of a rare circulating cell may increase the rigidity of the cell, and therefore, make it less likely the fixed rare circulating cell will be able to pass through a pore having a diameter smaller than a diameter of the cell, which can increase recovery.

In one aspect, a method for isolating or enriching rare circulating cells from a sample can include fixing one or more rare circulating cells in a sample. In some embodiments, rare circulating cells can include circulating tumor cells, epithelial progenitor cells, stem cells, mesenchymal cells, fetal cells, or combinations of these cell types. In some embodiments, rare circulating cells can include circulating tumor cells. In some embodiments, circulating tumor cells can originate from a carcinoma, sarcoma, leukemia, lymphoma, myeloma or nervous system cancer. In a preferred embodiment, circulating tumor cells can originate from a carcinoma, for example, a basal cell carcinoma, a squamous cell carcinoma, a renal cell carcinoma, an invasive ductal carcinoma or an adenocarcinoma.

In some embodiments, a sample can be a blood sample, for example, a whole blood sample, a plasma sample or a serum sample. In some embodiments, a sample can be a lymph fluid sample. In some embodiments, a sample can be from a subject, for example, a mammal, preferably, a human.

In some embodiments, fixing one or more rare circulating cells in a sample can include adding a fixative to a sample. In some embodiments, a fixative can include an aldehyde, for example, formaldehyde, glutaraldehyde, or paraformaldehyde. In a preferred embodiment, a fixative can include formaldehyde.

In some embodiments, fixing one or more rare circulating cells in a sample can include adding a fixative to the sample so that a concentration of the fixative in the sample can be at least 0.05% w/v, at least 0.10% w/v, at least 0.15% w/v, at least 0.20% w/v, or at least 0.25% w/v. In some embodiments, fixing one or more rare circulating cells in a sample can include adding a fixative to the sample so that a concentration of the fixative in the sample can be at most 0.40% w/v, at most 0.35% w/v, at most 0.30% w/v, at most 0.25% w/v, or at most 0.20% w/v. In some embodiments, fixing one or more rare circulating cells in a sample can include adding a fixative to the sample so that a concentration of the fixative in the sample can be 0.05-0.35% w/v, preferably, 0.1-0.3% w/v, more preferably, about 0.25% w/v.

In some embodiments, fixing one or more rare circulating cells in a sample can include adding at least 50 µL, at least 100 µL, at least 150 µL, at least 200 µL, at least 250 µL, at least 500 µL or at least 1 mL of a fixative to the sample. In some embodiments, fixing one or more rare circulating cells in a sample can include adding at most 2 mL, at most 1.5 mL, at most 1 mL, at most 500 µL, at most 250 µL, or at most 100 µL of a fixative to the sample. In some embodiments, fixing one or more rare circulating cells in a sample can include adding 50-500 µL, preferably, 20-500 µL, of a fixative to the sample.

In some embodiments, fixing one or more rare circulating cells in a sample can include incubating the sample with a fixative. In some embodiments, a sample can be incubated with a fixative for at least 30 seconds, at least 1 minute, at least 2 minutes, at least 5 minutes, or at least 10 minutes. In some embodiments, a sample can be incubated with a fixative for at most 30 minutes, at most 25 minutes, at most 20 minutes, at most 15 minutes, or at most 10 minutes. In some embodiments, a sample can be incubated with a fixative for 1-20 minutes, preferably, 3-10 minutes.

In some embodiments, fixing the one or more rare circulating cells can create a fixed sample (i.e., a sample that includes one or more fixed rare circulating cells).

In some embodiments, a method for isolating rare circulating cells from a sample can comprise isolating one or more rare circulating cells from a sample using a size exclusion technique. In some embodiments, a method for enriching rare circulating cells from a sample can comprise enriching rare circulating cells in a sample using a size exclusion technique. For example, one or more rare circulating cells can be isolated or enriched by directing a fixed sample through one or more filter membranes. In some embodiments, one or more filter membranes can be part of a microfiltration device. In some embodiments, at least one of the one or more filter membranes can have a pore size of at least 5 microns, at least 6 microns, at least 7 microns, at least 8 microns, at least 9 microns, or at least 10 microns. In some embodiments, at least one of the one or more filter membranes can have a pore size of at most 12 microns, at most 11 microns, at most 10 microns, at most 9 microns, at most 8 microns, at most 7 microns, or at most 6 microns. In some embodiments, at least one of the one or more filter membranes can have a pore size of between 5 and 10 microns, preferably, between 7 and 9 microns, more preferably 8 microns.

In one aspect, a method of analyzing rare circulating cells in a sample include fixing one or more rare circulating cells in a sample. In some embodiments, rare circulating cells can include circulating tumor cells, epithelial progenitor cells, stem cells, mesenchymal cells, fetal cells, or combinations of these cell types. In some embodiments, rare circulating cells can include circulating tumor cells. In some embodiments, circulating tumor cells can originate from a carcinoma, sarcoma, leukemia, lymphoma, myeloma or nervous system cancer. In a preferred embodiment, circulating tumor cells can originate from a carcinoma, for example, a basal cell carcinoma, a squamous cell carcinoma, a renal cell carcinoma, an invasive ductal carcinoma or an adenocarcinoma.

In some embodiments, a sample can be a blood sample, for example, a whole blood sample, a plasma sample or a serum sample. In some embodiments, a sample can be a lymph fluid sample. In some embodiments, a sample can be from a subject, for example, a mammal, preferably, a human.

In some embodiments, fixing one or more rare circulating cells in a sample can include adding a fixative to the sample. In some embodiments, a fixative can include an aldehyde, for example, formaldehyde, glutaraldehyde, or paraformaldehyde. In a preferred embodiment, a fixative can include formaldehyde.

In some embodiments, fixing one or more rare circulating cells in a sample can include adding a fixative to the sample so that a concentration of the fixative in the sample can be at least 0.05% w/v, at least 0.10% w/v, at least 0.15% w/v, at least 0.20% w/v, or at least 0.25% w/v. In some embodiments, fixing one or more rare circulating cells in a sample can include adding a fixative to the sample so that a concentration of the fixative in the sample can be at most 0.40% w/v, at most 0.35% w/v, at most 0.30% w/v, at most 0.25% w/v, or at most 0.20% w/v. In some embodiments, fixing one or more rare circulating cells in a sample can include adding a fixative to the sample so that a concentration of the fixative in the sample can be 0.05-0.35% w/v, preferably, 0.1-0.3% w/v, more preferably, about 0.25% w/v.

In some embodiments, fixing one or more rare circulating cells in a sample can include adding at least 50 µL, at least 100 µL, at least 150 µL, at least 200 µL, at least 250 µL, at least 500 µL or at least 1 mL of a fixative to the sample. In some embodiments, fixing one or more rare circulating cells in a sample can include adding at most 2 mL, at most 1.5 mL, at most 1 mL, at most 500 µL, at most 250 µL, or at most 100 µL of a fixative to the sample. In some embodiments, fixing one or more rare circulating cells in a sample can include adding 50-500 µL, preferably, 20-500 µL, of a fixative to the sample.

In some embodiments, fixing one or more rare circulating cells in a sample can include incubating the sample with a fixative. In some embodiments, a sample can be incubated with a fixative for at least 30 seconds, at least 1 minute, at least 2 minutes, at least 5 minutes, or at least 10 minutes. In some embodiments, a sample can be incubated with a fixative for at most 30 minutes, at most 25 minutes, at most 20 minutes, at most 15 minutes, or at most 10 minutes. In some embodiments, a sample can be incubated with a fixative for 1-20 minutes, preferably, 3-10 minutes.

In some embodiments, fixing the one or more rare circulating cells can create a fixed sample.

In some embodiments, a method of analyzing rare circulating cells in a sample can comprise enriching or isolating one or more rare circulating cells from a sample. In some embodiments, one or more rare circulating cells can be isolated or enriched using a size exclusion technique. For example, one or more rare circulating cells can be isolated or enriched by directing a fixed sample through one or more filter membranes. In some embodiments, one or more filter membranes can be part of a microfiltration device. In some embodiments, at least one of the one or more filter membranes can have a pore size of at least 5 microns, at least 6 microns, at least 7 microns, at least 8 microns, at least 9 microns, or at least 10 microns. In some embodiments, at least one of the one or more filter membranes can have a pore size of at most 12 microns, at most 11 microns, at most 10 microns, at most 9 microns, at most 8 microns, at most 7 microns, or at most 6 microns. In some embodiments, at least one of the one or more filter membranes can have a pore size of between 5 and 10 microns, preferably, between 7 and 9 microns, more preferably 8 microns.

In some embodiments, a method of analyzing rare circulating cells in a sample can include performing an analysis of one or more rare circulating cells. In some embodiments, performing an analysis of one or more rare circulating cells can include staining, dyeing, immunocytochemistry, immunohistochemistry, in situ hybridization, PCR, single cell sequence analysis, cell sorting, cell counting, microscopy or a combination these techniques.

In one aspect, a composition can include one or more rare circulating cells and a fixative.

In some embodiments, rare circulating cells can include circulating tumor cells, epithelial progenitor cells, stem cells, mesenchymal cells, fetal cells, or combinations of these cell types. In some embodiments, rare circulating cells can include circulating tumor cells. In some embodiments, circulating tumor cells can originate from a carcinoma, sarcoma, leukemia, lymphoma, myeloma or nervous system cancer. In a preferred embodiment, circulating tumor cells can originate from a carcinoma, for example, a basal cell carcinoma, a squamous cell carcinoma, a renal cell carcinoma, an invasive ductal carcinoma or an adenocarcinoma.

In some embodiments, a sample can be a blood sample, for example, a whole blood sample, a plasma sample or a serum sample. In some embodiments, a sample can be a lymph fluid sample. In some embodiments, a sample can be from a subject, for example, a mammal, preferably, a human.

In some embodiments, a fixative can include an aldehyde, for example, formaldehyde, glutaraldehyde, or paraformaldehyde. In a preferred embodiment, a fixative can include formaldehyde.

In some embodiments, a concentration of fixative in a composition can be at least 0.05% w/v, at least 0.10% w/v, at least 0.15% w/v, at least 0.20% w/v, or at least 0.25% w/v. In some embodiments, a concentration of fixative in a composition can be at most 0.40% w/v, at most 0.35% w/v, at most 0.30% w/v, at most 0.25% w/v, or at most 0.20% w/v. In some embodiments, a concentration of fixative in a composition can be 0.05-0.35% w/v, preferably, 0.1-0.3% w/v, more preferably, about 0.25% w/v.

DEFINITIONS

Figure 1:
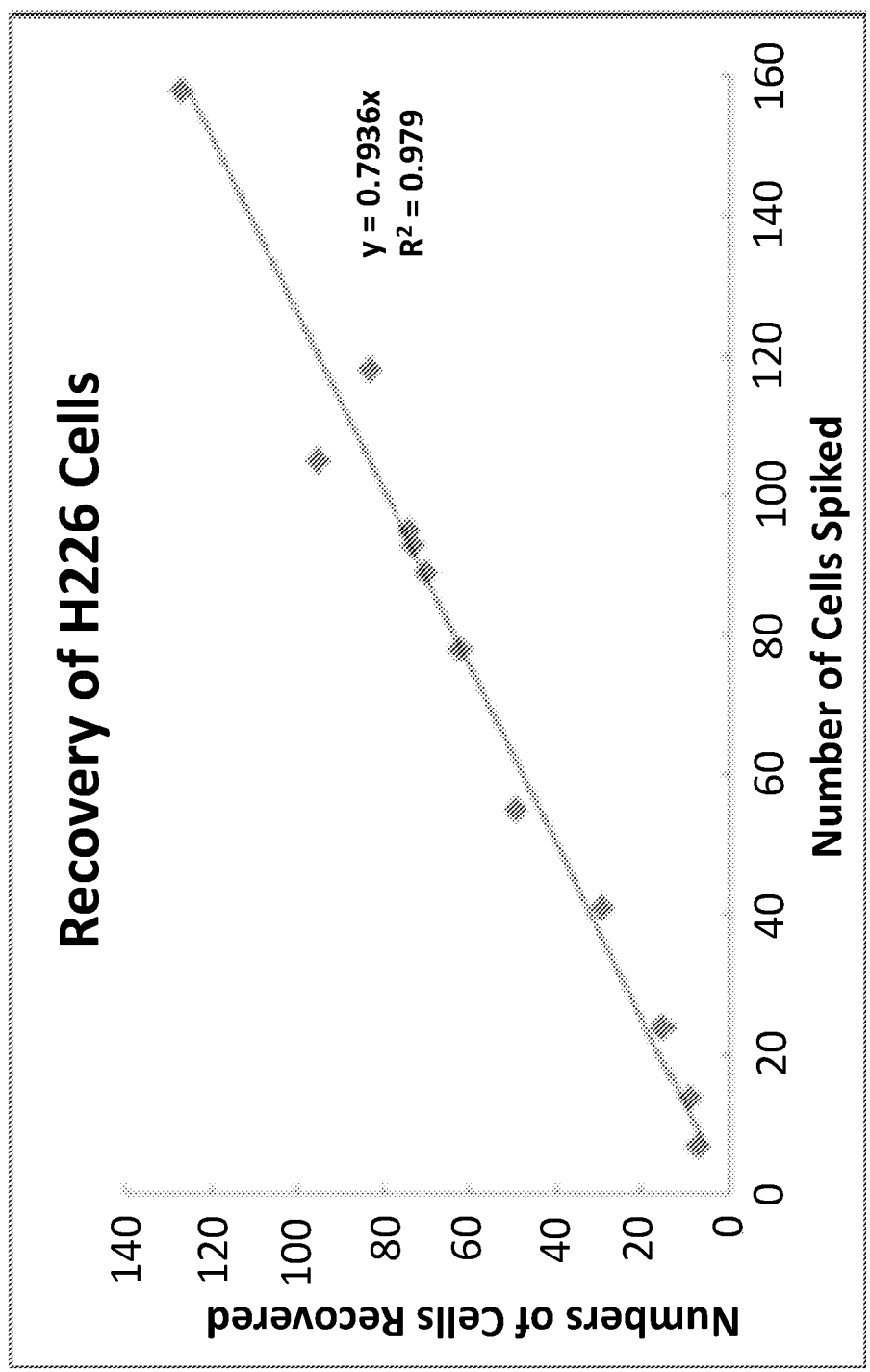
FIG. 1 is a graph showing a recovery of NCI-H226 cells with 0.2% formaldehyde pretreatment. Freshly trypsinized H226 cells were spiked into whole blood collected with customized Transfix® tubes and including a formaldehyde pretreatment. After performing a circulating tumor cell (CTC) isolation and detection process, NCI-H226 cells retained on a filtration membrane were counted, which is reflected on the graph.

About: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Enrich: As used herein, "enrich" or "enriching" refers to a process of increasing the concentration or proportion of rare circulating cells in a sample. In other words, a concentration or proportion of rare circulating cells in a sample can be greater at a second time point than a concentration or proportion of rare circulating cells in a sample at a first time point. For instance, "enriching" can include removing one or more components from a sample, e.g., reducing the volume of a sample without a concomitant reduction in the amount of rare circulating cells, which can be achieved, e.g., by size exclusion techniques such as filtration.

Isolate: As used herein, "isolate" or "isolating" refers to a process of separating rare circulating cells from at least one other component in a sample. Isolated rare circulating cells may be separated from about 40%, about 50%, about 60%, about 70%, about 80%, about 90%, about 91%, about 92%, about 93%, about 94%, about 95%, about 96%, about 97%, about 98%, about 99%, or more than about 99% of other components in a sample. In some embodiments, isolated rare circulating cells can be about 80%, about 85%, about 90%, about 91%, about 92%, about 93%, about 94%, about 95%, about 96%, bout 97%, about 98%, about 99%, or more than about 99% pure. As used herein, a substance is "pure" if it is substantially free of other components.

Rare circulating cells: As used herein, "rare circulating cells" refer to cells that can be found with a frequency on the order of 100 cells or less per mL of a sample of a subject, for example, a blood or lymph fluid sample. Examples of rare circulating cells can include circulating tumor cells, circulating epithelial progenitor cells, circulating stem cells, circulating mesenchymal cells, and circulating fetal cells. More specifically, examples of rare circulating cells of a solid tumor can include circulating tumor cells, cancer stem cells, and cells that are migrating to a tumor (e.g., due to chemoattraction) such as circulating endothelial progenitor cells, circulating endothelial cells, circulating pro-angiogenic myeloid cells, and circulating dendritic cells. Circulating tumor cells, for instance, can be generally found with a frequency of 1-10 circulating tumor cells per mL of blood. Similarly, circulating fetal cells can be typically found with a frequency of 1-10 circulating fetal cells per mL of blood.

DETAILED DESCRIPTION

It has been known that rare circulating cells can be found in biological fluids, such a blood and lymph fluid. For example, it has been known for over a century that circulating tumor cells (CTCs) are shed into the vasculature system from a primary tumor and circulate in bloodstreams to distant sites to form metastasis. Rare circulating cells in biological fluids can be obtained from in a non-invasive way (e.g., by a blood draw). In the case of CTCs, isolating these cells from a biological fluid and analyzing CTCs can provide significant amount of information for a better understanding, e.g., of tumor biology. In this way, CTCs in a blood sample can be used as a "liquid biopsy" to follow patients over time. In the case of circulating fetal cells, isolating these cells from a mother's blood and analyzing them can provide important genetic information about a developing fetus, for example, the presence of aneuploidy. However, detection, enumeration and molecular characterization of rare circulating cells has been challenging as rare circulating cells are, as their name suggests, rare. For example, the frequencies of CTCs found in peripheral blood of metastatic patients has been on the order of 1-10 CTC per mL. In comparison, 1 mL of blood contains millions of white blood cells and billions of red blood cells. For this reason, isolation or enrichment of rare circulating cells from biological fluids can be important for examining them.

Generally, rare circulating cells isolation and enrichment methods can be categorized to two classes:

1) Isolation or Enrichment Strategies Based on Biological Properties

Examples of biological properties used in isolation or enrichment methods can include cell surface biomarkers. This type of enrichment strategy is employed in the only FDA approved CTC in vitro diagnostic system, Cell-Search™. While this type of strategy has seen some success, rare circulating cells, including CTCs, can be highly heterogeneous and do not necessarily express, e.g., the same biomarker. As such, techniques based on biological properties are limited to enriching or isolating cells that include a preselected biological property, and therefore, necessarily fail to retain cells that lack the preselected biological property. Consequently, rare circulating cells with unexpected or unique biological properties, e.g., may not be enriched or isolated using these techniques.

2) Isolation or Enrichment Strategies Based on the Physical Properties

Examples of isolation or enrichment strategies based on physical properties include, but not limited to, density gradients and size exclusion techniques, e.g., filtration through a pore having a particular size. For example, Siemen's automated CTC platform (Integrated Cell Capture Micro-Device or ICCMD) utilizes filtration and size to capture CTCs. An ICCMD platform can filter milliliters of blood through one or more 8 um filter membranes and can retain CTCs on the one or more filters for downstream analysis. This method relies on the larger size of CTCs (e.g., around 30 µM in the case of breast cancer cells) compared to the majority of blood cells, which can range from 8 to 12 µM. However, cells are elastic, and cells (including rare circulating cells) can still pass through a pore having a diameter smaller than that of the cell. For instance, Coumans, et al., reported that a 15 µm cell can easily pass through a 5 µm pore while a 6 µm rigid bead does not pass through a 5 µm pore. (Coumans, et al., "Filtration parameters influencing circulating tumor cell enrichment from whole blood," PLoS One, 8(4), Apr. 26, 2013, which is incorporated by reference in its entirety). Rare circulating cells that pass through a smaller diameter may not retained, and if that occurs, recovery of rare circulating cells can be compromised.

As current techniques for enriching or isolating rare circulating cells from a sample based on biological properties (e.g., cell surface markers) are limited by the heterogeneity of biological properties of rare circulating cells, and current techniques for enriching or isolating rare circulating cells from a sample based on physical properties (e.g., size) are hindered by the flexibility of rare circulating cells, there is a need for a method that can be applied regardless of the biological properties of the rare circulating cells and can attenuate the impact of cell flexibility on recovery rates.

Without being bound to any particular theory, methods and compositions described herein can fulfill a need in the art, as the methods and compositions increase the rigidity of rare circulating cells by fixation, which permits the use of techniques for the separation of rare circulating cell based on physical properties (e.g., size) with a high retention rate.

Samples Including Rare Circulating Cells

Rare circulating cells are cells that are found in biological fluids in extremely low numbers (i.e., 100 cells or less per mL of fluid sample). Typically, rare circulating cells are present in these low numbers because they are not normally found in the particular biological fluid, but rather, are present in the fluid as a result of an abnormal condition (e.g., cancer, disease, pregnancy, etc.). Examples of rare circulating cells can include circulating tumor cells, circulating epithelial progenitor cells, circulating stem cells, circulating mesenchymal cells, and circulating fetal cells.

Rare circulating cells can be present in a sample, most often a biological fluid that originated from a subject. A subject can be a human, but can be include another mammal such as, e.g., another primate, a rodent, a canine, a feline, an equine, an ovine, or a porcine. A sample can include, without limitation, whole blood, plasma, serum, red blood cells, white blood cells (e.g., peripheral blood mononuclear cells), cord blood, saliva, urine, stool (i.e., feces), sputum, bronchial lavage fluid, tears, nipple aspirate, lymph fluid, bone marrow, amniotic fluid, spinal and pleural effusion, any other bodily fluid, and cellular extracts thereof. In some embodiments, a sample can be whole blood or a fractional component thereof, such as plasma, serum, or a cell pellet.

A sample can be obtained by any technique known in the art. For example, lymph fluid can be collected using a needle to draw fluid from a lymph node or during a lymph node biopsy. As another example, a blood sample can be collected by an intravenous blood draw.

Historically, a significant proportion of biological samples have been collected in one place and transported to another place for analysis. Accordingly, once a sample has been obtained, the sample may need to be transported and/or stored. Consequently, a sample may be added to a storage solution at the time the sample is obtained from a subject. For example, when blood is collected, it can be placed in a collection tube that can include, among other things, a stabilizer (e.g., ethylenediaminetetraacetic acid (EDTA)), an anticoagulant (e.g., heparin, citrate dextrose, oxalate), an antimicrobial agent, a protease inhibitor, a buffer, a low amount (i.e., less than 0.05% w/v) of a fixative, and combinations of these agents. Typically, a sample may be stored in a refrigerator (e.g., about 4° C.) for up two weeks or frozen (e.g., about −20° C. or less) for up to 2 months before it degrades to a point beyond which optimal results may not be obtained when conducting analyses on the sample.

Fixation of Rare Circulating Cells

Methods for enriching or isolating rare circulating cells, as described herein, include fixing one or more rare circulating cells in a sample. In some embodiments, fixing one or more rare circulating cells in a sample can create a fixed sample (i.e., a sample that includes one or more fixed rare circulating cells). Fixing preserves cell structure and can increase cell rigidity. Fixing can be achieved by various techniques, including physical methods (e.g., heating, micro-waving and cryo-preservation (i.e., freezing)) or chemical methods (e.g., addition of an alcohol or an aldehyde). There are two primary mechanisms by which chemical fixation occurs: denaturation and cross-link formation. Denaturation can be induced by dehydrants, such as alcohols or acetone. These reagents can remove and replace free water in cells and tissues, which can render water soluble proteins insoluble. Non-coagulant fixing agents (e.g., aldehydes) can chemically react with proteins and other cell and tissue components and can become bound to them by addition and formation of inter-molecular and intra-molecular cross-links. In preferred embodiments, non-coagulant fixing agents can be used to fix rare circulating cells. In some instances, a fixative can include an aldehyde, for example, formaldehyde, glutaraldehyde, or paraformaldehyde.

In some embodiments, a fixative can be added to a sample. In some embodiments, a fixative can be added to a sample so that a concentration of the fixative in the sample equals a desired amount. For example, a concentration of fixative in a sample can be at least 0.05% w/v, at least 0.10% w/v, at least 0.15% w/v, at least 0.20% w/v, or at least 0.25% w/v. In some embodiments, a concentration of fixative in a sample can be at most 0.40% w/v, at most 0.35% w/v, at most 0.30% w/v, at most 0.25% w/v, or at most 0.20% w/v. In some embodiments, a concentration of fixative in a sample can be 0.05-0.35% w/v, preferably, 0.1-0.3% w/v, more preferably, about 0.25% w/v.

In certain circumstances, a predetermined amount of a fixative can be added to a sample. In some embodiments, at least 50 µL, at least 100 µL, at least 150 µL, at least 200 µL, at least 250 µL, at least 500 µL or at least 1 mL of a fixative can be added to a sample. In some embodiments, at most 2 mL, at most 1.5 mL, at most 1mL, at most 500 µL, at most 250 µL, or at most 100 µL of a fixative can be added to a sample. In some embodiments, 50-500 µL, preferably, 20-500 µL, of a fixative can be added to a sample.

In some embodiments, fixing one or more rare circulating cells in a sample can include incubating the sample with a fixative. In some embodiments, a sample can be incubated with a fixative for at least 30 seconds, at least 1 minute, at least 2 minutes, at least 5 minutes, or at least 10 minutes. In some embodiments, a sample can be incubated with a fixative for at most 30 minutes, at most 25 minutes, at most 20 minutes, at most 15 minutes, or at most 10 minutes. In some embodiments, a sample can be incubated with a fixative for 1-20 minutes, preferably, 3-10 minutes.

In some embodiments, fixing one or more rare circulating cells in a sample can include incubating the sample with a fixative at a temperature of at least 0° C., at least 10° C., at least 20° C., at least 30° C., or at least 40° C. In some embodiments, fixing one or more rare at least circulating cells in a sample can include incubating the sample with a fixative at a temperature of at most 75° C., at most 60° C., at most 50° C., at most 40° C., at most 30° C., or at most 20° C. In some embodiments, fixing one or more rare at least circulating cells in a sample can include incubating the sample with a fixative at a temperature of 0° C.-40° C., 20° C.-30° C., or about room temperature.

When fixing one or more rare circulating cells in a sample, an amount of fixative, an incubation time and an incubation temperature can each influence the degree of fixation. Generally, adding more fixative to a sample, increasing an incubation time, and/or increasing an incubation temperature will increase the amount of fixation. Therefore, an increase in an incubation time may be able to compensate for a decreased amount of fixative in a sample. Conversely, an increase in an amount of fixative in a sample may be able to compensate for a decreased incubation time.

For rare circulating cells in a sample, however, a high degree of fixation may not be desirable, as it can result in over-crosslinking of sample components, which can in turn clog filtration devices, for example. Therefore, in some embodiments, balancing these factors can be important for successful enrichment or isolation of rare circulating cells from a sample.

In some embodiments, fixing one or more rare circulating cells in a sample can include incubating the sample with a fixative (e.g., formaldehyde) at 20-30° C. for at most 10 minutes, where a concentration of fixative in a sample can be 0.1-0.35% w/v. In some embodiments, fixing one or more rare circulating cells in a sample can include incubating the sample with a fixative (e.g., formaldehyde) at 20-30° C. for at most 30 minutes, where a concentration of fixative in a sample can be 0.05-0.30% w/v.

In some cases, a fixative is added with other agents, such as a saline solution (e.g., phosphate buffered saline), to a sample. A saline solution can be added to a sample prior to a fixative to dilute the sample. A saline solution can be a buffer. In some embodiments, the pH of a sample (with or without a fixative and/or a saline solution) can be between pH 4 and pH 9, preferably, between pH 7 and pH 8.

Fixation can also be influenced by storage of a sample. For example, a blood sample that has been stored under refrigeration for a longer period of time (e.g., more than 5 days, more than 1 week or more than 2 weeks) in a storage solution, particularly one with a low concentration (i.e., less than 0.05%) of a fixative may be incubated with either a lower fixative concentration (e.g., 0.05-0.30% w/v, 0.05-0.20% w/v or 0.05-0.15% w/v) and/or for a shorter time (e.g., at most 15 minutes, at most 10 minutes, at most 5 minutes, or at most 2 minutes).

In some embodiments, fixing one or more rare circulating cells in a sample to create a fixed sample can include fixing 50% or more, 60% or more, 70% or more, 80% or more, or 90% or more of rare circulating cells in the sample. A level of fixation can be quantified using a number of techniques known in the art. For example, microscopy methods have been used in previous studies to evaluate the performance of fixation methods, including light microscopy (St-Laurent, et al. (2006)), reflection contrast microscopy (Hoetelmans, et al. (2001)), fluorescence microscopy (Celie, et al. (2005)), Raman microscopy (Meade, et al. (2010)), electron microscopy (Hoetelmans, et al. (2001)), as well as atomic force microscopy (Moloney, et al. (2004)). Atomic force microscopy (AFM) has been widely used in all fields of surface science since its invention in 1986, including microbiological studies (Bolshakova, et al. (2004)). (St-Laurent, et al., "Comparison of cell fixation methods of induced sputum specimens: an immunocytochemical analysis," J Immunol Methods, 308(1-2):36-42, Jan. 20, 2006; Hoetelmans, et al., "Effects of acetone, methanol, or paraformaldehyde on cellular structure, visualized by reflection contrast microscopy and transmission and scanning electron microscopy," Appl Immunohistochem Mol Morphol, 9(4):346-51, Dec. 2001; Celie, et al., "Effect of fixation protocols on in situ detection of L-selectin ligands," J Immunol Methods, 298 (1-2):155-9, Mar. 2005; Bonnier, et al., "Imaging live cells grown on a three dimensional collagen matrix using Raman microspectroscopy," Analyst, 135(12):3169-772010, December 2010; Moloney, et al., "Atomic force microscopy analysis of enveloped and non-enveloped viral entry into, and egress from, cultured cells," Ultramicroscopy, 100(3-4):163-9, August 2004; Bolshakova, et al., "Microbial surfaces investigated using atomic force microscopy," Biotechnol Prog., 20(6):1615-22, November-December 2004, each of which is incorporated by reference in its entirety).

Enrichment and/or Isolation of Rare Circulating Cells

Once one or more rare circulating cells in a sample have been fixed, the one or more fixed rare circulating cells can be enriched or isolated. Preferably, enrichment or isolation can be achieved using a size exclusion technique, which can enrich or isolate rare circulating cells independent of the level of heterogeneity within these cells. An example, of a size exclusion technique that can be utilized is filtration. In some embodiments, enriching or isolating one or more rare circulating cell can be performed by directing a fixed sample, including one or more fixed rare circulating cells, through one or more filter membranes.

A filter membrane can be made of any material that is compatible with rare circulating cells and/or a fixed sample. For example, a filter membrane should be made of a material that does not bind or otherwise interact with components of a fixed sample. Additionally, a filter membrane should be made of a material that will not chemically degrade in the presence of a component of a fixed sample. A filter membrane material can, for example, be made from a fibrous material, such as synthetic fibers (e.g., polyester or polypropylene), semi-synthetic fibers, regenerated fibers, or inorganic fibers. Examples of suitable filter membrane materials can include cellulose acetate, nylon, polyethersulfone, regenerated cellulose, silicon, glass, polydimethyl siloxane, polyurethane, polyimide, polycarbonate, polytetrafluoroethylene, and a metal (e.g., palladium). A filter membrane can include wetting agents, which should also be compatible with rare circulating cells and/or a fixed sample.

A filter membrane can include one or more pores. A pore size of a filter membrane can be less than a diameter of a rare circulating cell that is being enriched or isolated. In some embodiments, a filter membrane (e.g., at least one of one or more filter membranes) can have a pore size that is less than 50%, less than 40%, less than 30% or less than 25% of a diameter of a rare circulating cell that is being enriched or isolated. For example, a filter with an 8 micron pore size can be used to enrich or isolate circulating cancer cells that have a diameter of about 30 microns.

In some embodiments, a filter membrane (e.g., at least one of one or more filter membranes) can have a pore size of at least 5 microns, at least 6 microns, at least 7 microns, at least 8 microns, at least 9 microns, or at least 10 microns. In some embodiments, a filter membrane (e.g., at least one of one or more filter membranes) can have a pore size of at most 12 microns, at most 11 microns, at most 10 microns, at most 9 microns, at most 8 microns, at most 7 microns, or at most 6 microns. In some embodiments, a filter membrane (e.g., at least one of one or more filter membranes) can have a pore size of between 5 and 10 microns, preferably, between 7 and 9 microns, more preferably 8 microns.

In some embodiments, one or more filter membranes can include a capture hole (i.e., pocket). A capture hole can have a size of at least 20 microns, at least 25 microns, at least 30 microns, at least 40 microns or at least 50 microns. A capture hole can have a size of at most 75 microns, at least 60 microns, at least 50 microns, or at least 40 microns. A pore can be included at the base of a capture hole.

Filter membranes can include pores of different sizes. For example, in some embodiments, a first filter membrane can have a first pore size and a second filter membrane can have a second pore size. In some embodiments, a first filter membrane can include a first pore having a first pore size and a second pore having a second pore size. Combinations of these embodiments can be utilized.

One or more filter membranes can be part of a filtration device, for example, a microfiltration device. In some instances, one or more filter membranes can be part of a filter unit of a filtration device. A microfiltration device can also include, for example, a reservoir, a control unit and/or a waste outlet. A control unit can control the flow of a sample through a filtration device. A control unit can include, for example, a valve, a pump, or a constrictor. In some cases, a control unit can be an influx control unit. In some cases, a control unit can be an efflux control unit.

Isolating one or more rare circulating cell can be performed by directing a fixed sample, including one or more fixed rare circulating cells, through one or more filter membranes. Directing a fixed sample through one or more filter membranes can result in retention of at least 60%, at least 70%, at least 80%, at least 90%, or at least 95% of rare circulating cells in the sample on the one or more filter membranes.

A variety of analyses can be performed on enriched or isolated rare circulating cells. Examples of analyses include staining, dyeing, immunocytochemistry, immunohistochemistry, in situ hybridization, PCR, single cell sequence analysis, cell sorting, cell counting, microscopy or combination of these techniques.

EXAMPLES

Example 1: Methods

A pretreatment method, including fixation, for filtration of rare circulating cells from a blood sample was developed. In an exemplary method, blood was collected from a subject and put in a TransFix® blood collection for transport and storage. Prior to filtration, the collected blood sample was transferred into a conical tube. The original blood collection tube was rinsed with a saline buffer to collect any residual cells, and the saline buffer was poured into the same conical tube as the collected blood sample. After bringing up the total volume to 20 mL with saline buffer, 250 µL of 16% formaldehyde was added to the diluted blood sample to achieve a final formaldehyde concentration of approximately 0.2% w/v. The conical tube was pulse vortexed for 3 seconds and incubated at room temperature for 5 minutes to fix the cells. The conical tube with the fixed blood sample was then loaded onto an Integrated Cell Capture Micro-Device (ICCMD) filtration system including an eight (8) micron filter. Isolated circulating tumor cells were collected for further processing.

Example 2: Determination of Percent Cell Recovery

Blood samples were collected from subjects, as described in Example 1. The blood samples were then spiked with various known amounts of NCI-H226 (a lung cancer cell line) cells and pre-treated according to the method provided in Example 1. The fixed, spiked samples were loaded onto an ICCMD filtration system. NCI-H226 cells retained on the filter were stained and counted. As shown in FIG. 1, there was a linear correlation between the number of NCI-H226 cells spiked into each blood sample and the number of NCI-H226 cells recovered from each blood sample. Comparison of the number of NCI-H226 cells spiked into each blood sample to the number of NCI-H226 cells recovered from each blood sample demonstrates that approximately 80% of recovery was achieved when the pretreatment method was utilized. The data represented an improvement over prior methodologies that do not include a fixative pretreatment, which generally have recovery rates of about 40-60% for spiked NCI-H226 cells (see, e.g., bar representing 0% w/v fixative in FIG. 2).

Example 3: Optimization of Percent Fixative

Figure 2:
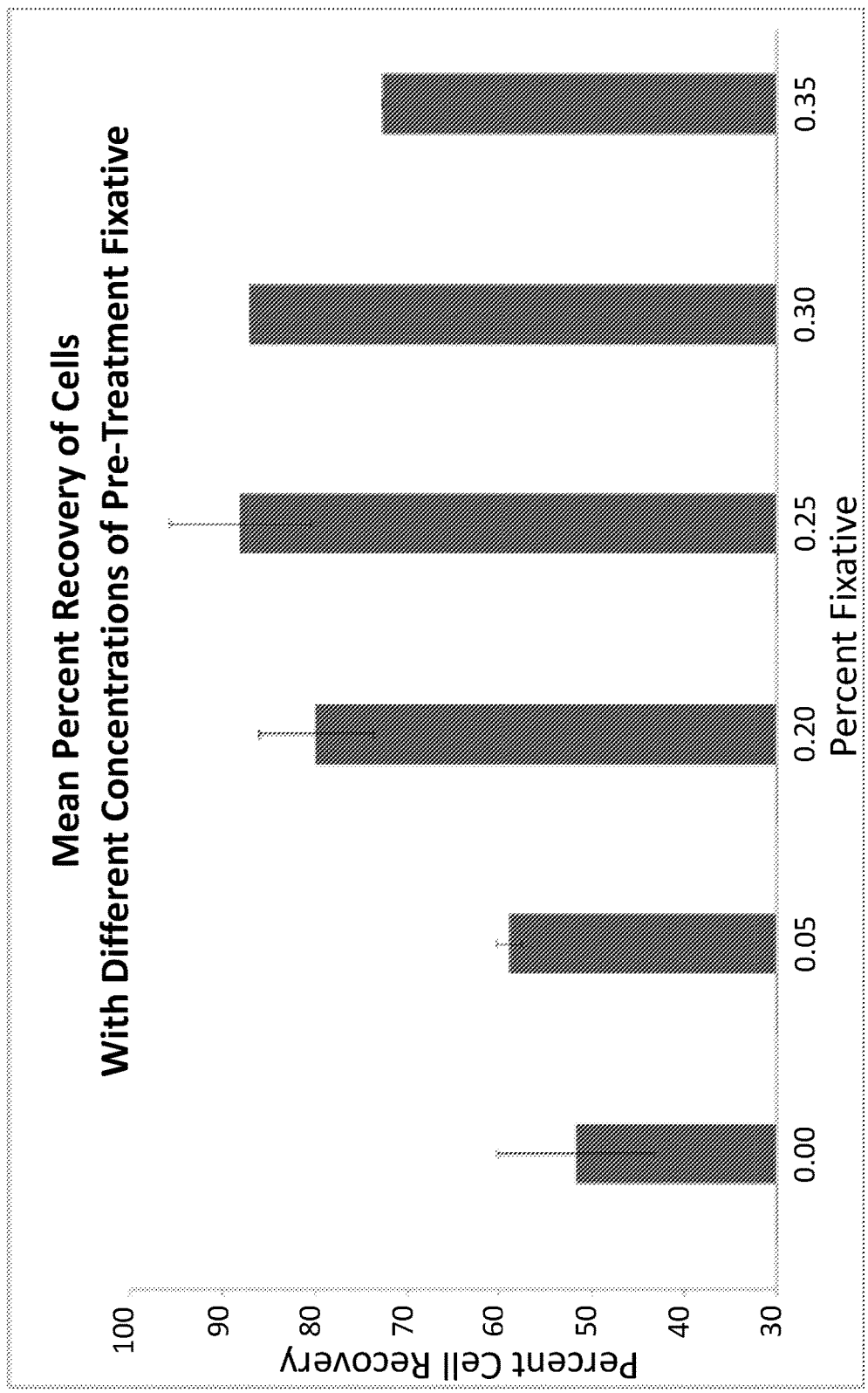
FIG. 2 is a bar chart showing a recovery of NCI-H226 cells with indicated concentrations of formaldehyde pretreatment. Mean values with 95% confidence bars are shown for conditions that were successfully tested in multiple replicates. No error bars are shown for single data points.

Various concentrations of fixative were tested to determine optimal concentrations of fixative for achieving an increased recovery of rare circulating cells (e.g., circulating tumor cells) from blood samples. Blood samples were collected from subjects, as described in Example 1. Each of the blood samples was spiked with the same known amount of NCI-H226 cells. The spiked blood samples were then pretreated as described in Example 1 using different concentrations of formaldehyde. The samples were loaded onto an ICCMD filtration system, and NCI-H226 cells retained on the filter were stained and counted. As shown in FIG. 2, the control sample, to which fixative was not added, showed a recovery rate of approximately 52%. Adding fixative improved the recovery rate, with the sample including 0.25% w/v formaldehyde showing the highest recovery rate (~87%). While two other higher concentrations, 0.3% w/v and 0.35% w/v, showed improved recovery rates over the control sample, use of 0.3% w/v and 0.35% w/v resulted in failure about half the time, possibly due to clogging of the filtration system. Without being bound to any theory, a possible reason for improved recovery of cancer cells is that an optimized fixation increases the rigidity of the cancer cells, which in turn increases retention of those cells above the pores of the membrane.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

All patents, applications, and publications cited in the text above are incorporated herein by reference.

What is claimed is:

1. A method for isolating rare circulating cells from a blood sample of a subject, comprising:
   fixing one or more rare circulating cells in a blood sample to create a fixed blood sample, wherein fixing the one or more rare circulating cells in the blood sample comprises adding an aldehyde to the blood sample so that the concentration of the aldehyde in the blood sample is 0.05-0.35% w/v; and
   isolating the one or more rare circulating cells by directing the fixed blood sample through one or more filter membranes.

2. The method of claim 1, wherein the rare circulating cells are circulating tumor cells.

3. The method of claim 2, wherein the circulating tumor cells originated from a carcinoma, sarcoma, leukemia, lymphoma, myeloma or nervous system cancer.

4. The method of claim 3, wherein the circulating tumor cells originated from a carcinoma.

5. The method of claim 1, wherein the subject is a mammal.

6. The method of claim 1, wherein the subject is a human.

7. The method of claim 1, wherein the aldehyde is formaldehyde, glutaraldehyde, or paraformaldehyde.

8. The method of claim 1, wherein the aldehyde is formaldehyde.

9. The method of claim 1, wherein fixing the one or more rare circulating cells in the blood sample comprises adding the aldehyde to the blood sample so that the concentration of the aldehyde in the blood sample is 0.1-0.3% w/v.

10. The method of claim 1, wherein fixing the one or more rare circulating cells in the blood sample comprises adding the aldehyde to the blood sample so that the concentration of the aldehyde in the blood sample is about 0.25% w/v.

11. The method of claim 1, wherein fixing the one or more rare circulating cells in the blood sample comprises incubating the blood sample with the aldehyde for 1-20 minutes.

12. The method of claim 1, wherein fixing the one or more rare circulating cells in the blood sample comprises incubating the blood sample with the aldehyde for 3-10 minutes.

13. The method of claim 1, wherein the one or more filter membranes are part of a microfiltration device.

14. The method of claim 1, wherein at least one of the one or more filter membranes has a pore size between 5 and 10 microns.

15. A method of enriching rare circulating cells in a blood sample of a subject, comprising:
- fixing one or more rare circulating cells in the blood sample to create a fixed blood sample, wherein fixing the one or more rare circulating cells in the blood sample comprises adding an aldehyde to the blood sample so that the concentration of the aldehyde in the blood sample is 0.05-0.35% w/v; and
- enriching the one or more rare circulating cells by directing the fixed blood sample through one or more filter membranes.

* * * * *